United States Patent
Hamatsu et al.

[11] Patent Number: 5,810,732
[45] Date of Patent: Sep. 22, 1998

[54] BONE ASSESSMENT APPARATUS

[75] Inventors: Natsuru Hamatsu; Naoki Ohtomo, both of Mitaka, Japan

[73] Assignee: Aloka Co., Ltd., Mitaka

[21] Appl. No.: 759,726

[22] Filed: Dec. 6, 1996

[30] Foreign Application Priority Data

Dec. 11, 1995 [JP] Japan .................................. 7-321460

[51] Int. Cl.⁶ .................................................. A61B 8/00
[52] U.S. Cl. .......................................... 600/449; 600/459
[58] Field of Search ........................ 128/661.03, 660.06, 128/660.01, 660.02, 662.03; 601/2, 4; 600/437, 442, 438, 449, 459

[56] References Cited

U.S. PATENT DOCUMENTS

| | | |
|---|---|---|
| 3,521,876 | 7/1970 | Smith . |
| 3,847,141 | 11/1974 | Hoop . |
| 5,036,855 | 8/1991 | Fry et al. ............................ 128/660.03 |
| 5,065,761 | 11/1991 | Pell ..................................... 128/660.03 |
| 5,134,999 | 8/1992 | Osipov ................................ 128/661.03 |
| 5,327,912 | 7/1994 | Mally . |
| 5,343,863 | 9/1994 | Wiener et al. ..................... 128/661.03 |
| 5,348,009 | 9/1994 | Ohtomo et al. . |
| 5,452,722 | 9/1995 | Langton ............................. 128/661.03 |
| 5,535,750 | 7/1996 | Matsui et al. ..................... 128/661.03 |
| 5,615,681 | 4/1997 | Ohtomo et al. ................... 128/661.03 |

FOREIGN PATENT DOCUMENTS

| | | |
|---|---|---|
| 0 576 217 A1 | 12/1993 | European Pat. Off. . |
| 2 091 448 | 1/1972 | France . |
| 7-204205 | 8/1995 | Japan . |
| 2 257 253 | 6/1993 | United Kingdom . |

*Primary Examiner*—Francis Jaworski
*Attorney, Agent, or Firm*—Fishman, Dionne, Cantor & Colburn

[57] ABSTRACT

A bone assessment apparatus for assessing bone by ultrasonic waves. A slider mechanism for supporting a platform is provided such that it is free to be given a parallel displacement. When a foot is placed on the platform and a pair of measuring units are brought close together, the platform starts to slide from when one of the units comes in contact with the foot. When the contact pressures of the two units are identical, the sliding motion stops. The center line of the foot is thereby made to coincide with the center line between transducers, and in this situation, ultrasonic waves are transmitted and received.

6 Claims, 2 Drawing Sheets

BONE ASSESSMENT APPARATUS

BACKGROUND OF THE INVENTION

1. Field of the Invention

This invention relates to a bone assessment apparatus, and more particularly to an improvement of a platform for mounting a part of a subject's body.

2. Description of the Prior Art

In recent years, bone assessment apparatus for assessing bone in living organism using ultrasonic waves or electromagnetic waves (e.g. X rays) have come into practical use.

A conventional bone assessment apparatus is mentioned in Japanese Patent Laid-Open Hei 6-22960. According to this apparatus, both ultrasonic wave and X rays are passed through bone, and the bone is assessed from their measured values. U.S. Pat. No. 3,847,141 discloses an apparatus for assessing bone using ultrasonic waves, and similar apparatus are mentioned in European Patent Laid-Open No. 0,576,217.

In these conventional apparatus, to assess the bone in a foot, the foot is placed on a fixed platform, and the distance between a pair of ultrasonic transducers provided on either side of the platform is narrowed. Eventually, the foot is gripped by the pair of transducers, and ultrasonic waves are transmitted from one transducer to the other (as in for example, Japanese Patent Laid-Open Hei 7-204205).

The pair of ultrasonic transducers are brought up equally from either side towards the center of the fixed platform on which the foot is placed.

However, when the foot is not correctly positioned in the center of the platform, a problem arises. In such a case when the foot is offset to the left or right on the platform and the transducers are brought up equally from either side, one transducer will press too much on the foot while the other transducer does not even come into contact with it. Even when both transducers come into contact with the foot, a suitable contact pressure cannot be obtained. The subject may then experience discomfort, and as the contact pressure affects the accuracy of ultrasonic measurement, a precise assessment cannot be made.

In some cases, pressure may be applied only to one side of the foot (heel), so a problem will arise when the foot is turned. This problem is shown in FIG. 3. When measuring units 10A and 10B are brought closer together, pressure is applied only to one side of a heel of a foot 100 which is not centrally placed on a platform 12, so the foot 100 rotates, and a precise bone assessment cannot be made.

This problem is not exclusive to bone assessment apparatus using ultrasonic measurement, and has also been mentioned with regard to other types of bone assessment apparatus (e.g. using X rays) where a living organism is gripped between a pair of measuring units, and with regard to an apparatus having only one measuring unit.

SUMMARY OF THE INVENTION

This invention was conceived in view of the above problem. It aims to provide a solution to the foregoing problem caused by a displacement of a body part to be examined on the platform.

This invention further aims to provide a solution to such a problem in a bone assessment apparatus where a pair of measuring units are brought up equally from either side towards the center of a body part to be examined.

It is therefore an object of this invention to automatically correct for a displacement when the body part is offset to some extent so that both measuring units still apply a suitable pressure and a precise measurement can be made.

To achieve the above object, this invention provides a bone assessment apparatus comprising:

a platform on which a body part to be examined is placed, a least one measuring unit disposed adjacent to said platform for performing measurements for assessing bone in said body part, an adjusting mechanism for adjusting the distance between said measuring unit and said body part in order to bring said measuring unit into contact with said body part, and a moving mechanism for moving said platform.

To achieve the above object, this invention is characterized in comprising:

a platform for mounting a body part to be examined, a pair of measuring units which send and receive measuring waves for assessing bone in the body part, an adjusting mechanism which adjusts the distance between the measuring units so as to grip the body part from both sides, and a slider which supports the platform so that the platform can move parallel to the alignment direction of the pair of measuring units.

According to the above construction, as the platform is supported by the slider so that it is free to slide, any displacement of the body part, for example to the left or right, can be cancelled out by sliding the platform.

In other words, when the adjusting mechanism is operated so that the measuring units are brought closer together, and only the unit on the side to which the body part is displaced comes in contact with the body part, the platform and body part are pushed towards the other side thereby giving them a parallel displacement, and consequently the body part comes in contact with the other measuring unit at the same contact pressure. Hence even if the body part is displaced on the platform, it can be brought in contact with both measuring units at a suitable contact pressure. This resolves the problem of unequal contact pressure of the measuring units.

In a preferred aspect of this invention, the measuring units comprise ultrasonic transducers which send and receive ultrasonic waves.

Also in a preferred aspect of this invention, the body part to be examined is a foot of a living organism and the platform is a foot platform.

DESCRIPTION OF THE PREFERRED EMBODIMENTS

Figure 1:
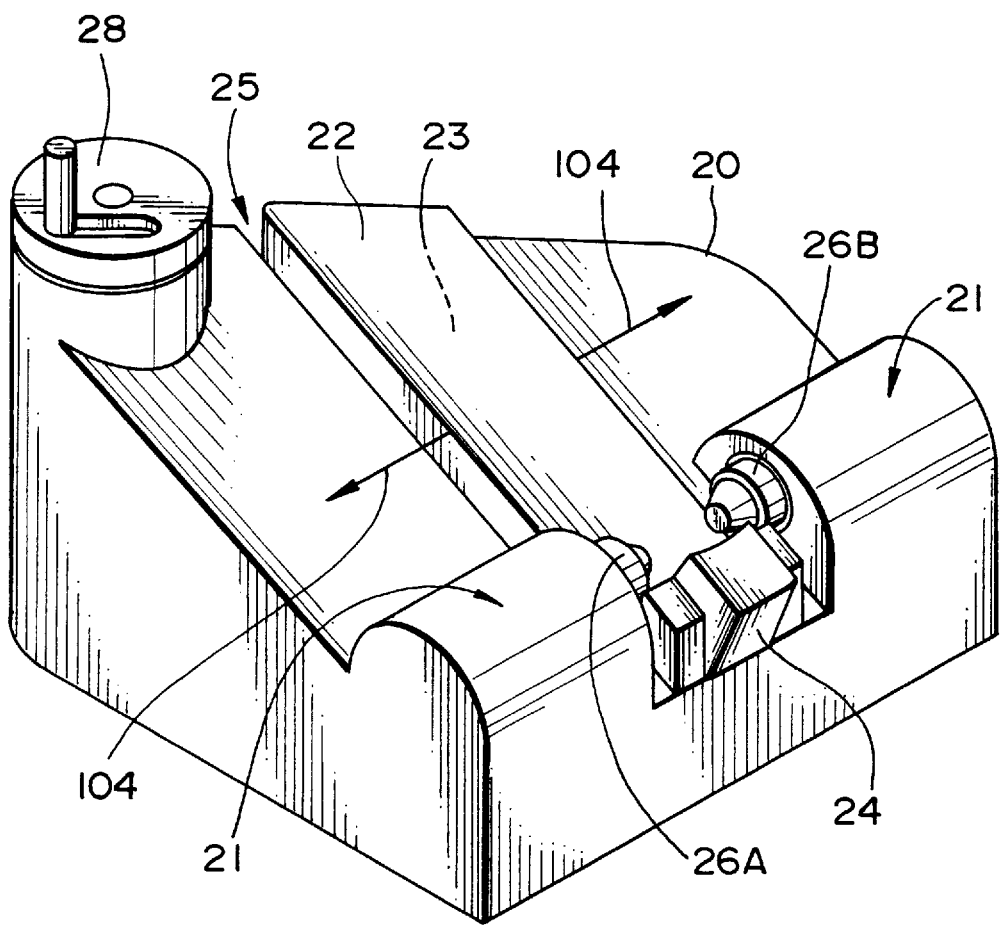
FIG. 1 is a perspective view showing measuring device according to this invention.

FIG. 1 shows a bone assessment apparatus according to this invention. The apparatus broadly comprises a controller and measuring device. A perspective view of the measuring device is shown in FIG. 1.

A platform 22, which is a foot platform, is obliquely disposed in the upper part of a chassis 20. A groove 25 for accommodating the platform 22 is formed in the chassis 20. The width of this groove 25 is wider than that of the platform 22. Specifically, the width of this groove 25 is set taking account of a slide amount of the platform 22 described hereafter. A heel grip 24 is formed in the lower part of the platform 22, and the cross-section of the platform 22 is therefore L-shaped. A foot may be placed on the platform 22 so that the undersurface of the heel is in contact with the heel grip 24.

The pair of measuring units 26A, 26B are disposed on either side of the platform 22 such that they are free to move. The measuring units 26A, 26B comprise internal ultrasonic transducers. These ultrasonic transducers send and receive ultrasonic waves to diagnose the integrity of a bone. The measuring units 26A, 26B comprise projecting contact walls formed from an elastic material. The contact walls are filled with an acoustic propagation fluid such as for example water.

A handle 28 is fitted to the chassis 20. When this handle 28 is rotated, the pair of measuring units 26A, 26B approach each other. The chassis 20 is provided with a distance adjusting mechanism 21. Using the handle 28 and the mechanism 21, the pair of measuring units 26A, 26B may be displaced equally towards or away from the center of the length between the units 26A, 26B. The mechanism 21 comprises a torque limiter, not shown, for maintaining the contact pressure between the contact walls and a foot (body part to be examined) at a predetermined value. This torque limiter is interposed between the handle 28 and the measuring units 26A, 26B. The torque limiter transmits a torque when the torque is less than a predetermined value, but stops transmission of drive force from the handle 28 when the torque value reaches the predetermined value.

The measuring device shown in FIG. 1 comprise a slider mechanism 23 which supports the platform 22 such that it is free to slide in the alignment direction of the units 26A, 26B. In FIG. 1, the operation of the slider mechanism 23 is denoted by a symbol 104. The slide direction 104 of the platform 22 coincide with the alignment direction of the pair of units 26A, 26B, and also coincides with the displacement direction of the units 26A, 26B.

The platform 22 may be freely given a parallel displacement (translation) a predetermined distance (e.g. ±2 cm) to the left and right of a reference center position. According to this embodiment, the slider mechanism 23 comprises one or more rails disposed parallel to the slide direction, and a plurality of rollers which roll on this rail. However, any mechanism may be used for the slider 23 provided it is capable of giving the platform 22 a parallel displacement to the left or right.

The operation of the measuring device shown in FIG. 1 will now be described.

First, a foot which is to be examined is placed on the platform 22. Normally, the subject positions the foot so that its center line coincides with the center line of the platform 22.

After making these preparations, when the handle 28 is rotated, the pair of measuring units 26A, 26B are made to approach the sides of the foot so that the heel of the foot is gripped by the pair of units 26A, 26B. When a certain contact pressure has been obtained, the torque limiter operates to interrupt transmission from the handle 28. In this state, even when the handle is rotated further, the contact pressure does not increase and is maintained at a certain value.

When the pair of measuring units are suitably in contact with the heel of the foot, ultrasonic waves are transmitted from the unit 26A to the other unit 26B, and traverse the foot (specifically, the heel bone). The propagation speed of sound in the bone and the attenuation of the ultrasonic wave may then be measured. The controller, not shown, calculates a bone assessment value based on the measured results. When the handle is rotated in the reverse direction, the torque limiter again transmits drive torque, and the pair of measuring units 26A, 26B move apart.

Figure 2:
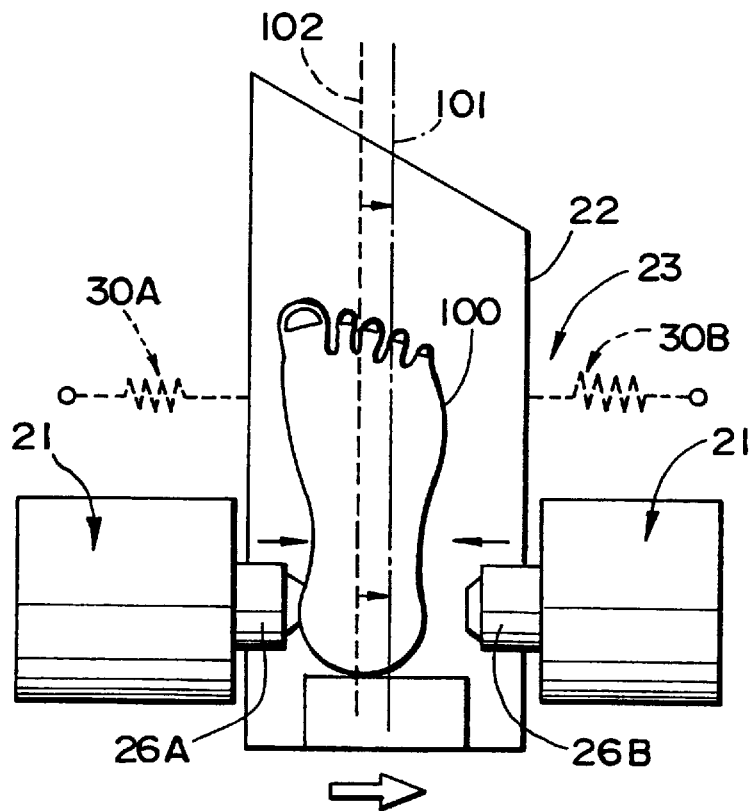
FIG. 2 is a diagram describing the operation of a slider according to this invention.
Figure 3:
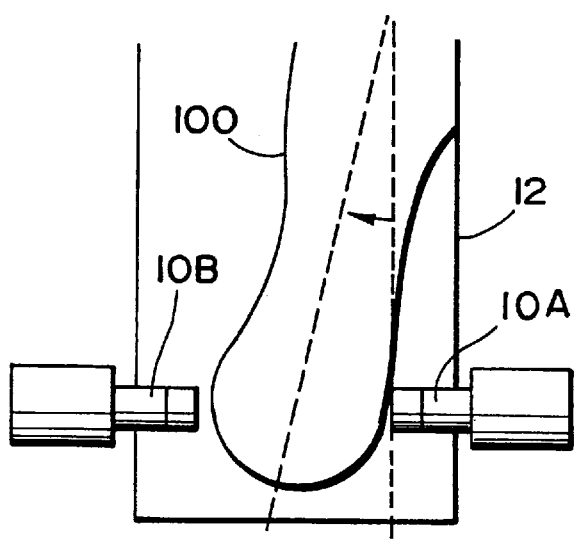
FIG. 3 is a diagram describing the problems inherent in the prior art.

However when a foot is placed in an offset position on the platform 22, the center line 101 between the transducers and the center line 102 of the foot do not coincide as shown in FIG. 2. In such a case, the slider mechanism 23 operates so that the discrepancy between the two center lines 101, 102 is very simply and automatically corrected.

Specifically, when the foot is positioned so that the center line 102 of the foot is offset relative to the center line 101 between the transducers as shown in FIG. 2, and the handle 28 shown in FIG. 1 is operated to bring the pair of measuring units 26A, 26B together, the unit 26A, for example, touches the heel first. In this situation, the pressure on contact is directly converted to a sliding motion of the platform 22 by the slider mechanism 23. The platform 22 continues to slide with the foot on it until the center line 102 of the foot coincides with the center line 101 between the transducers, i.e. until the contact pressure of the unit 26B is the same as that of the unit 26A.

After or at the same time when the two center lines 101, 102 coincide and the contact pressure reaches the predetermined value, the torque limiter operates as described heretofore. In this situation, the contact pressures of the measuring units 26A, 26B are identical and coincide with the predetermined value. If ultrasonic waves are then transmitted and received, measurements may be made with high precision, and the reliability of the bone assessment value which is finally obtained is improved.

When the subject places a foot on the platform 22, he need thus be concerned only with the direction in which it is pointing. In other words, there is no need to take care that the center line 102 of the foot coincides exactly with the center line 101 between the transducers, and less effort is therefore required.

According to the aforesaid embodiment, the slider mechanism 23 supports the platform 22 such that it is free to move to the left and right. A center aligning mechanism having a weakly elastic action may also be provided to ensure that the center line of the platform 22 which is free to slide coincides with the center line 101 between the transducers.

When there is no foot on the platform 22, the center aligning mechanism constantly exerts a weak force on the platform 22 so that the platform 22 is always positioned at a reference position (center).

This center aligning mechanism may for example comprise springs 30A, 30B on either side of the platform 22 as shown by the broken lines in FIG. 2. The springs 30A and 30B have an identical spring force, and their forces are exerted in mutual opposition to one another.

This center aligning mechanism therefore resolves problems due to the initial displacement of the platform 22 to one side. It will of course be understood that the elastic force of the springs 30A, 30B should be a weak spring force of such a degree that the motion of the units 26A, 26B is not impeded.

Hence according to this invention, in a bone assessment apparatus comprising a mechanism for bringing the pair of measuring units 26A, 26B equally together from either side towards the center of a body part to be examined, a slider mechanism 23 is provided which supports the platform 22 such that it is free to be given a parallel displacement (translation).

Therefore, even when the body part is placed on the platform 22 such that it is slightly offset to the left or right, this offset is automatically corrected, both of the measuring units 26A, 26B are maintained at a suitable contact pressure, and a precise measurement can be made.

The aforementioned slider mechanism 23 may be provided in a bone assessment apparatus in which only one of the pair of measuring units is free to move while the other is fixed.

Also, the above-mentioned slider mechanism 23 may be provided in a bone assessment apparatus in which only one of the measuring units sends ultrasonic waves and receives reflected waves.

What is claimed is :

1. A bone assessment apparatus comprising;
   (a) a platform on which a body part to be examined is placed,
   (b) a pair of measuring units disposed on either side of said platform for sending and receiving waves for assessing bone in said body part, said measurement units and said body part platform being mounted on to a common base,
   (c) an adjusting mechanism for adjusting the distance between said pair of measuring units so that said body part is gripped from both sides by said pair of measuring units, and
   (d) a slider mechanism for supporting said platform such that it is free to be given a parallel displacement to the direction of said distance adjustment by a driving force provided by said adjusting mechanism and such that said displacement is relative to at least one of said measuring units and to said common base.

2. An apparatus as defined in claim 1, wherein the chassis of said apparatus has a groove formed therein for slidably accommodating said platform.

3. An apparatus as defined in claim 1, wherein said measuring units comprise ultrasonic transducers, and said pair of ultrasonic transducers transmit and receive ultrasonic waves.

4. An apparatus as defined in claim 1, wherein said body part to be examined is a foot of a living organism, and said platform is a platform on which said foot is to be placed.

5. An apparatus as defined in claim 1, wherein said platform further comprises a center aligning mechanism for positioning said platform in the center of said pair of measuring units.

6. An apparatus as defined in claim 5, wherein said aligning mechanism is a pair of elastic means, and said elastic means exert an identical elastic force in mutually opposite directions.

* * * * *